United States Patent [19]

Terahara et al.

[11] Patent Number: 4,479,965

[45] Date of Patent: Oct. 30, 1984

[54] M-4 AND ISOM-4 DERIVATIVES THEIR PREPARATION AND COMPOSITIONS CONTAINING THEM

[75] Inventors: Akira Terahara; Minoru Tanaka, both of Hiromachi, Japan

[73] Assignee: Sankyo Company, Limited, Tokyo, Japan

[21] Appl. No.: 372,696

[22] Filed: Apr. 28, 1982

[30] Foreign Application Priority Data

May 7, 1981 [JP] Japan .................................. 56-68646

[51] Int. Cl.³ ................. C07D 309/30; A61K 31/365
[52] U.S. Cl. .................................... 424/279; 549/292
[58] Field of Search ......................... 549/292; 424/279

[56] References Cited

U.S. PATENT DOCUMENTS 4,346,227 8/1982 Terahara et al. .................. 549/292
4,361,515 11/1982 Terahara et al. .................. 549/292

*Primary Examiner*—Norma S. Milestone
*Attorney, Agent, or Firm*—Frishauf, Holtz, Goodman & Woodward

[57] ABSTRACT

Tetrahydro-M-4 and tetrahydro-IsoM-4 hydroxy carboxylic acids of the formula (I):

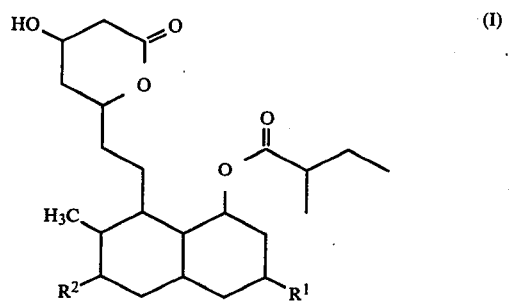

wherein one of $R^1$ and $R^2$ represents a hydrogen atom and the other represents a hydroxy group which are useful for inhibiting chloresterol biosynthesis in the liver. The invention also provides pharmaceutical compositions containing said lactone(s).

10 Claims, 3 Drawing Figures

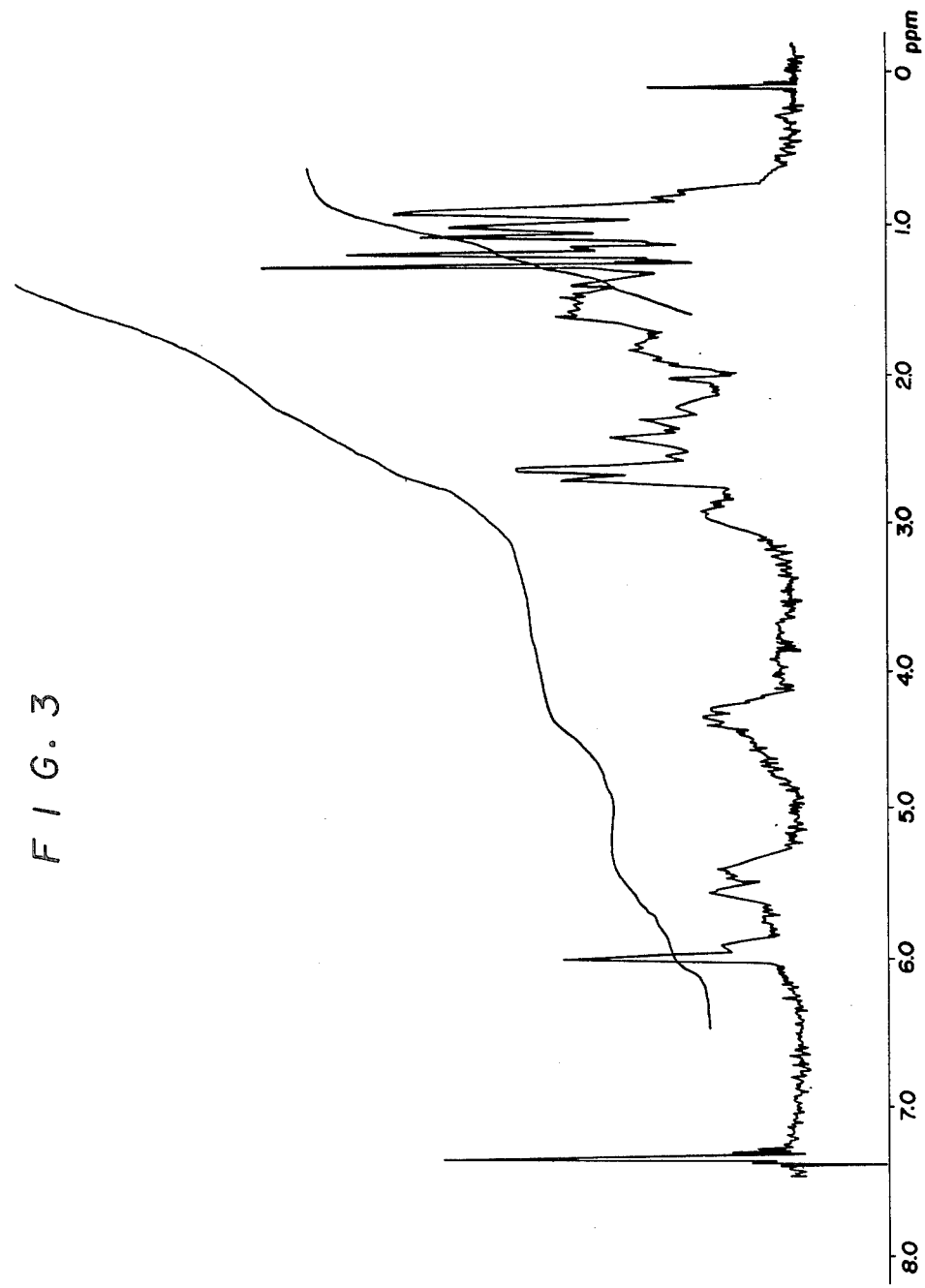
F I G. 3

M-4 AND ISOM-4 DERIVATIVES THEIR PREPARATION AND COMPOSITIONS CONTAINING THEM

BACKGROUND TO THE INVENTION

The present invention relates to a series of new derivatives of M-4 and IsoM-4, to processes for preparing them and to pharmaceutical compositions containing them.

M-4 and IsoM-4, which are described in U.S. patent application Ser. No. 270,846, filed June 5, 1981, to A. Terahara and M. Tanaka, which issued as Pat. No. 4,346,227 when in the form of their lactones, have the formulae:

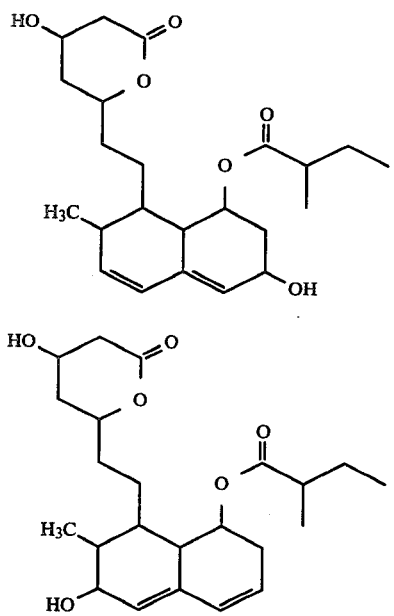

respectively. The formulae given above show the compounds in their lactone form; of course, under appropriate conditions, the lactone can be hydrated to give the corresponding hydroxy-carboxylic acid.

M-4 and IsoM-4 are amongst a number of compounds which may be derived from the group of compounds collectively designated ML-236 and described, for example, in U.S. Patent Specification No. 3,983,140. Other compounds having a similar structure and collectively designated MB-530 have been discovered and are described, for example, in United Kingdom Patent Specifications No. 2,046,737, No. 2,049,664 and No. 2,055,100, and derivatives of both the ML-236 and MB-530 compounds are described, for example, in United Kingdom Patent Specification No. 2,075,013. Of the many compounds there are known which have structures of the ML-236 or MB-530 type, most have shown some ability to inhibit the biosynthesis of cholesterol and some have shown this ability to a sufficient degree that they might be of value in the treatment of such disorders as hyperlipaemia (especially hypercholesteraemia) and arteriosclerosis.

We have now discovered a series of compounds which are derivatives of M-4 and IsoM-4 and which, whilst retaining the ability of their parent compounds to inhibit the biosynthesis of cholesterol, are far less readily deactivated in vivo than are the parent compounds.

BRIEF SUMMARY OF INVENTION

The compounds of the invention are tetrahydro M-4 and tetrahydro-IsoM-4 lactones which have the formula (I):

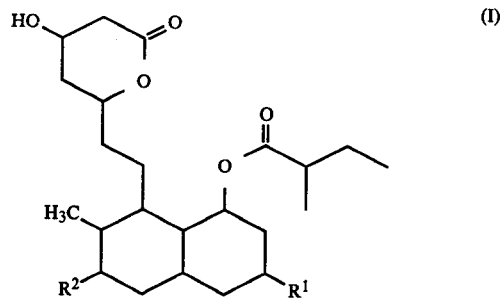

and their corresponding free carboxylic acids, which may be represented by formula (II):

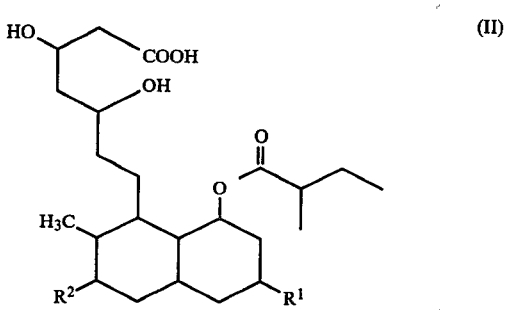

(in which one of $R^1$ and $R^2$ represents a hydrogen atom and the other represents a hydroxy group), and salts and esters of the carboxylic acids.

Those compounds of formulae (I) and (II) in which $R^1$ represents a hydroxy group and $R^2$ represents a hydrogen atom are collectively referred to as "tetrahydro-M-4" and those compounds of formulae (I) and (II) in which $R^1$ represents a hydrogen atom and $R^2$ represents a hydroxy group are collectively referred to as "tetrahydro-IsoM-4". The compounds of formula (I) are referred to as "tetrahydro-M-4 lactone" or "tetrahydro-IsoM-4 lactone" and the compounds of formula (II) are referred to as "tetrahydro-M-4 carboxylic acid" or "tetrahydro-IsoM-4 carboxylic acid".

The invention also provides processes for preparing tetrahydro-M-4 and tetrahydro-IsoM-4 by the catalytic reduction of M-4 or IsoM-4, respectively, and for the preparation of salts and esters by salification or esterification of tetrahydro-M-4 or tetrahydro-IsoM-4.

The invention also provides a pharmaceutical composition comprising an effective amount of an antihyperlipaemic agent in admixture with a pharmaceutically acceptable carrier or diluent, wherein the antihyperlipaemic agent is at least one compound selected from compounds of formula (I), compounds of formula (II) and salts and esters thereof.

DETAILED DESCRIPTION OF INVENTION

Figure 1:
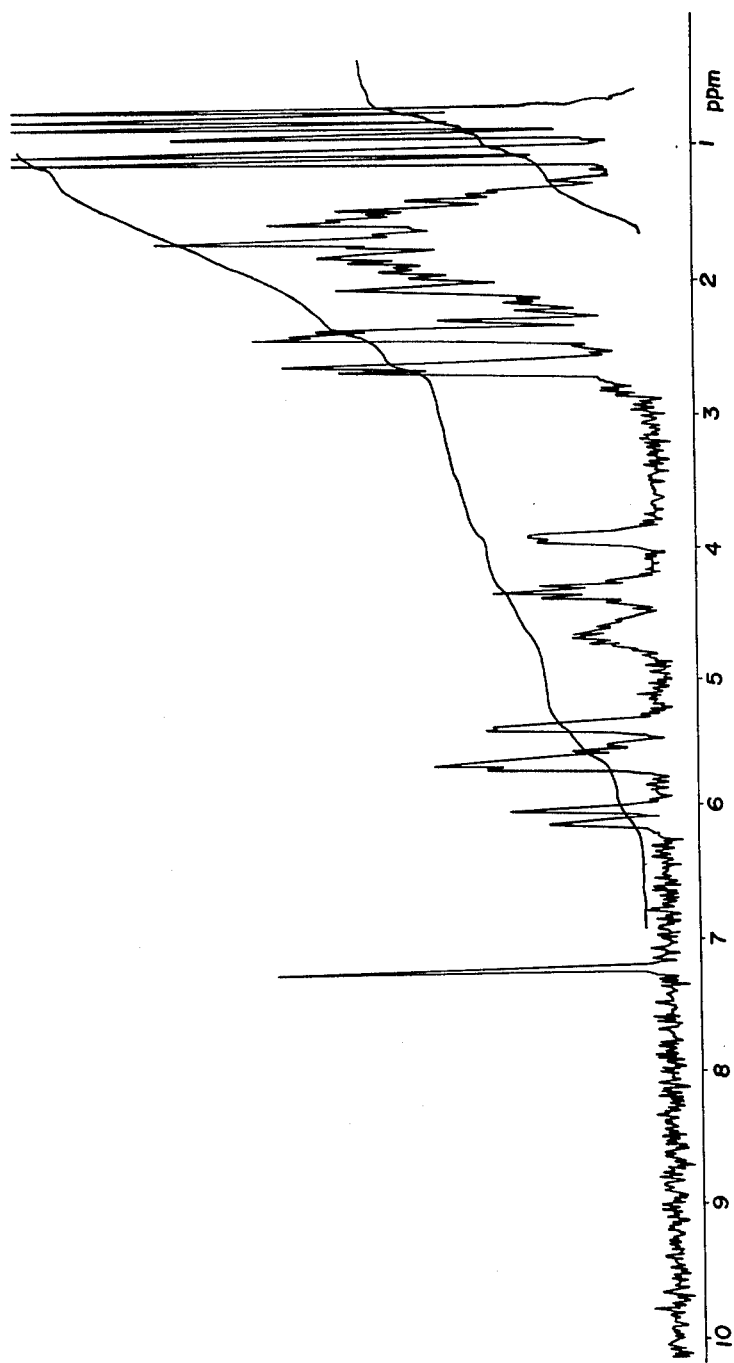

The salts of tetrahydro-M-4 or tetrahydro-IsoM-4 carboxylic acids may be metal salts, ammonium salts or salts with organic amines or amino acids.

Metal salts of tetrahydro-M-4 carboxylic acid and of tetrahydro-IsoM-4 carboxylic acid may be represented by formula (III):

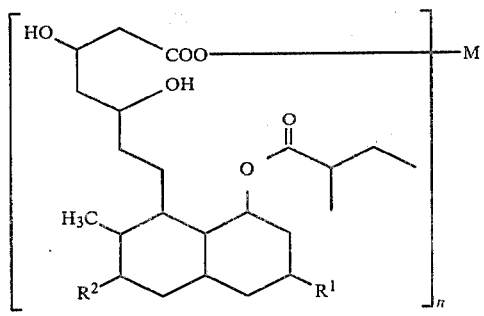

(in which $R^1$ and $R^2$ are as defined above, M represents a metal atom and n represents the valency of the metal atom). Examples of metals which may be represented by M in these salts include: alkali metals, such as sodium or potassium; alkaline earth metals, such as calcium; and other metals, such as magnesium, aluminium, iron, zinc, nickel or cobalt. Of these metals, the alkali metals, alkaline earth metals and aluminium are preferred, sodium, calcium and aliminium being most preferred.

The ammonium, organic amine and amino acid salts of tetrahydro-M-4 carboxylic acid and of tetrahydro-IsoM-4 carboxylic acid may be represented by formula (IV):

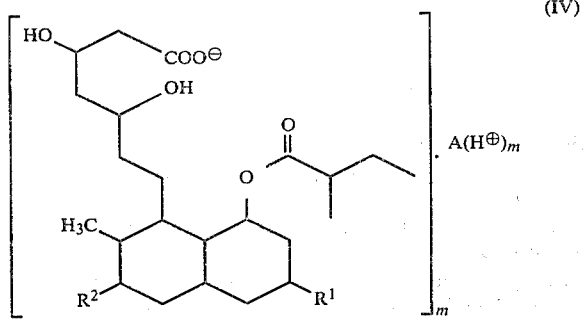

(in which $R^1$ and $R^2$ are as defined above, A represents ammonia, an amino acid or an organic amine, and m is an integer). The integer represented by m is preferably 1, that is to say the amine or amino acid represented by A is preferably monoacidic.

Examples of amino acids which may be represented by A in the above formula (IV) include such basic amino acids as arginine, lysine, histidine, 2,4-diaminobutyric acid, or ornithine.

When A represents an organic amine, it is preferably a monoamine and may be an aliphatic, aromatic, alicyclic, heterocyclic or carbohydrate monoamine. Examples include: primary alkylamines, such as octylamine, t-octylamine or 2-ethylhexylamine; primary, secondary and tertiary $C_7$ or $C_8$ aralkylamines, such as benzylamine, α-methylbenzylamine, phenethylamine, dibenzylamine, N-methylbenzylamine, N,N-dimethylbenzylamine, N,N-diethylbenzylamine, N-ethyl-N-methylbenzylamine or tribenzylamine; primary, secondary or tertiary $C_5$-$C_7$ saturated alicyclic amines, such as cyclopentylamine, cyclohexylamine, cycloheptylamine, N-methylcyclopentylamine, N-ethylcyclohexylamine, N-ethylcycloheptylamine, dicyclohexylamine, N,N-dimethylcyclopentylamine, N,N-dimethylcyclohexylamine or N,N-diethylcycloheptylamine; 5 or 6 membered heterocyclic amines having a single nitrogen atom as the hetero atom, such as pyrrolidine, N-methylpyrrolidine, piperidine or N-methylpiperidine; morpholine; $C_1$-$C_3$ alkyl esters of aliphatic or aromatic amino acids, such as leucine methyl ester, diethyl glutamate, phenylglycine ethyl ester, β-phenylalanine propyl ester or β-phenylalanine methyl ester; and amine derivatives of carbohydrates, such as glucosamine.

Where the amino acids and amines mentioned above can exist in the form of stereoisomers or optical isomers, it is possible to use any of the isomers or mixtures thereof.

Preferred amines are t-octylamine, benzylamine, dibenzylamine, N,N-dimethylbenzylamine, cyclohexylamine, dicyclohexylamine, N,N-dimethylcyclohexylamine, N-methylpyrrolidine, morpholine, L-leucine alkyl esters, dialkyl L-glutamates, D-phenylglycine alkyl esters and D-glucosamine; of which the most preferred amines are t-octylamine, dibenzylamine, dicyclohexylamine, morpholine, D-phenylglycine alkyl esters and D-glucosamine.

The esters of tetrahydro-M-4 carboxylic acid and of tetrahydro-IsoM-4 carboxylic acid may be represented by formula (V):

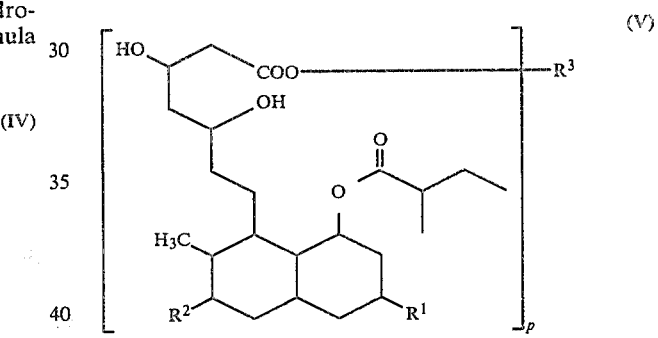

(in which $R^1$ and $R^2$ are as defined above, $R^3$ represents the alcoholic moiety of an ester and p represents the valency of $R^3$).

Where p represents 1, $R^3$ preferably represents an alkyl group, an unsubstituted benzyl group, a substituted benzyl group having at least one substituent selected from alkyl groups, alkoxy groups and halogen atoms, an unsubstituted phenacyl group or a substituted phenacyl group having at least one substituent selected from alkyl groups, alkoxy groups and halogen atoms.

Where $R^3$ represents an alkyl group, this may be a straight or branched chain group and preferably has from 1 to 6 carbon atoms. Examples of such a group include the methyl, ethyl, propyl, isopropyl butyl, pentyl and hexyl groups.

Where $R^3$ represents a benzyl group, this may be unsubstituted or substituted, the substituents preferably being $C_1$ or $C_2$ alkyl or alkoxy groups or halogen atoms. One or more, preferably one, substituents are possible and, if there is more than one substituent, these may be the same or different. Examples of such benzyl groups include the benzyl, 2-methylbenzyl, 3-methylbenzyl, 4-methylbenzyl, 2-ethylbenzyl, 3-ethylbenzyl, 4-ethylbenzyl, 2-methoxybenzyl, 3-methoxybenzyl, 4-methoxybenzyl, 2-ethoxybenzyl, 3-ethoxybenzyl, 4-ethoxybenzyl, 2-chlorobenzyl, 3-chlorobenzyl, 4- chlorobenzyl, 2-bromobenzyl, 3-bromobenzyl and 4-bromobenzyl groups.

R³ may represent an unsubstituted or substituted phenacyl group, in which the substituents are preferably C₁ or C₂ alkyl or alkoxy groups or halogen atoms. One or more, preferably one, substituents are possible and, where there is more than one substituent, these may be the same or different. Examples of such phenacyl groups include the phenacyl, 2-methylphenacyl, 3-methylphenacyl, 4-methylphenacyl, 2-ethylphenacyl, 3-ethylphenacyl, 4-ethylphenacyl, 2-methoxyphenacyl, 3-methoxyphenacyl, 4-methoxyphenacyl, 2-ethoxyphenacyl, 3-ethoxyphenacyl, 4-ethoxyphenacyl, 2-chlorophenacyl, 3-chlorophenacyl, 4-chlorophenacyl, 2-bromophenacyl, 3-bromophenacyl and 4-bromophenacyl groups.

Where p is 2, R³ represents a bivalent alcoholic moiety, preferably a C₂-C₆ alkylene or alkylidene group, for example, an ethylene, ethylidene, propylene, propylidene, trimethylene, tetramethylene, butylidene, pentamethylene or pentylidene group, as well as such groups having one or more substituents, e.g. hydroxy groups, halogen atoms, or trifluoromethyl groups.

Where p is 3, R³ represents a trivalent alcoholic moiety and it is preferably a saturated aliphatic hydrocarbon group having from 2 to 6 carbon atoms and optionally one or more substituents, e.g. hydroxy groups, halogen atoms or trifluoromethyl groups.

We prefer that p should be 1 and that R³ should represent an alkyl group (most preferably methyl, ethyl, propyl, isopropyl, butyl or hexyl), an optionally substituted benzyl group (most preferably benzyl, 4-methylbenzyl, 4-methoxybenzyl or 4-chlorobenzyl) or an optionally substituted phenacyl group (most preferably phenacyl, 4-methylphenacyl, 4-methoxyphenacyl or 4-bromophenacyl).

Representative examples of compounds of the invention are given in the following list:

1. Tetrahydro-M-4.
2. Tetrahydro-IsoM-4.
3. Sodium tetrahydro-M-4 carboxylate.
4. Sodium tetrahydro-IsoM-4 carboxylate.
5. Calcium di(tetrahydro-M-4 carboxylate).
6. Calcium di(tetrahydro-IsoM-4 carboxylate).
7. Aluminium tri(tetrahydro-M-4 carboxylate).
8. Aluminium tri(tetrahydro-IsoM-4 carboxylate).
9. Arginine tetrahydro-M-4 carboxylate.
10. Arginine tetrahydro-IsoM-4 carboxylate.
11. Lycine tetrahydro-M-4 carboxylate.
12. Lycine tetrahydro-IsoM-4 carboxylate
13. Histidine tetrahydro-M-4 carboxylate.
14. Histidine tetrahydro-IsoM-4 carboxylate.
15. The 2,4-diaminobutyric acid salt of tetrahydro-M-4.
16. The 2,4-diaminobutyric acid salt of tetrahydro-IsoM-4.
17. Ornithine tetrahydro-M-4 carboxylate.
18. Ornithine tetrahydro-IsoM-4 carboxylate.
19. t-Octylamine tetrahydro-M-4 carboxylate.
20. t-Octylamine tetrahydro-IsoM-4 carboxylate.
21. Dibenzylamine tetrahydro-M-4 carboxylate.
22. Dibenzylamine tetrahydro-IsoM-4 carboxylate.
23. Dicyclohexylamine tetrahydro-M-4 carboxylate.
24. Dicyclohexylamine tetrahydro-IsoM-4 carboxylate.
25. Morpholine tetrahydro-M-4 carboxylate.
26. Morpholine tetrahydro-IsoM-4 carboxylate.
27. Aluminium di(tetrahydro-M-4 carboxylate) hydroxide.
28. Aluminium di(tetrahydro-IsoM-4 carboxylate) hydroxide.
29. Glucosamine tetrahydro-M-4 carboxylate.
30. Glucosamine tetrahydro-IsoM-4 carboxylate.
31. The dimethyl glutamate salt of tetrahydro-M-4.
32. The diethyl glutamate salt of tetrahydro-M-4.
33. The dipropyl glutamate salt of tetrahydro-M-4.
34. The diisopropyl glutamate salt of tetrahydro-M-4.
35. The dibutyl glutamate salt of tetrahydro-M-4.
36. The di-sec-butyl glutamate salt of tetrahydro-M-4.
37. The di-t-butyl glutamate salt of tetrahydro-M-4.
38. The dipentyl glutamate salt of tetrahydro-M-4.
39. The diisopentyl glutamate salt of tetrahydro-M-4.
40. The di-t-pentyl glutamate salt of tetrahydro-M-4.
41. The dimethyl glutamate salt of tetrahydro-IsoM-4.
42. The diethyl glutamate salt of tetrahydro-IsoM-4.
43. The dipropyl glutamate salt of tetrahydro-IsoM-4.
44. The diisopropyl glutamate salt of tetrahydro-IsoM-4.
45. The dibutyl glutamate salt of tetrahydro-IsoM-4.
46. The di-sec-butyl glutamate salt of tetrahydro-IsoM-4.
47. The di-t-butyl glutamate salt of tetrahydro-IsoM-4.
48. The dipentyl glutamate salt of tetrahydro-IsoM-4.
49. The diisopentyl glutamate salt of tetrahydro-IsoM-4.
50. The di-t-pentyl glutamate salt of tetrahydro-IsoM-4.
51. Methyl tetrahydro-M-4 carboxylate.
52. Methyl tetrahydro-IsoM-4 carboxylate.
53. Ethyl tetrahydro-M-4 carboxylate.
54. Ethyl tetrahydro-IsoM-4 carboxylate.
55. Propyl tetrahydro-M-4 carboxylate.
56. Propyl tetrahydro-IsoM-4 carboxylate.
57. Isopropyl tetrahydro-M-4 carboxylate.
58. Isopropyl tetrahydro-IsoM-4 carboxylate.
59. Butyl tetrahydro-M-4 carboxylate.
60. Butyl tetrahydro-IsoM-4 carboxylate.
61. Hexyl tetrahydro-M-4 carboxylate.
62. Hexyl tetrahydro-IsoM-4 carboxylate.
63. Benzyl tetrahydro-M-4 carboxylate.
64. Benzyl tetrahydro-IsoM-4 carboxylate.
65. 4-Methylbenzyl tetrahydro-M-4 carboxylate.
66. 4-Methylbenzyl tetrahydro-IsoM-4 carboxylate.
67. 4-Methoxybenzyl tetrahydro-M-4 carboxylate.
68. 4-Methoxybenzyl tetrahydro-IsoM-4 carboxylate.
69. 4-Chlorobenzyl tetrahydro-M-4 carboxylate.
70. 4-Chlorobenzyl tetrahydro-IsoM-4 carboxylate.
71. Phenacyl tetrahydro-M-4 carboxylate.
72. Phenacyl tetrahydro-IsoM-4 carboxylate.
73. 4-Methylphenacyl tetrahydro-M-4 carboxylate.
74. 4-Methylphenacyl tetrahydro-IsoM-4 carboxylate.
75. 4-Methoxyphenacyl tetrahydro-M-4 carboxylate.
76. 4-Methoxyphenacyl tetrahydro-Is M-4 carboxylate.
77. 4-Bromophenacyl tetrahydro-M-4 carboxylate.
78. 4-Bromophenacyl tetrahydro-IsoM-4 carboxylate.
79. The methyl ester of phenylglycine tetrahydro-M-4 carboxylate.
80. The ethyl ester of phenylglycine tetrahydro-M-4 carboxylate.

81. The propyl ester of phenylglycine tetrahydro-M-4 carboxylate.
82. The isopropyl ester of phenylglycine tetrahydro-M-4 carboxylate.
83. The butyl ester of phenylglycine tetrahydro-M-4 carboxylate.
84. The sec-butyl ester of phenylglycine tetrahydro-M-4 carboxylate.
85. The t-butyl ester of phenylglycine tetrahydro-M-4 carboxylate.
86. The pentyl ester of phenylglycine tetrahydro-M-4 carboxylate.
87. The isopentyl ester of phenylglycine tetrahydro-M-4 carboxylate.
88. The t-pentyl ester of phenylglycine tetrahydro-M-4 carboxylate.
89. The methyl ester of phenylglycine tetrahydro-IsoM-4 carboxylate.
90. The ethyl ester of phenylglycine tetrahydro-IsoM-4 carboxylate.
91. The propyl ester of phenylglycine tetrahydro-IsoM-4 carboxylate.
92. The isopropyl ester of phenylglycine tetrahydro-IsoM-4 carboxylate.
93. The butyl ester of phenylglycine tetrahydro-IsoM-4 carboxylate.
94. The sec-butyl ester of phenylglycine tetrahydro-IsoM-4 carboxylate.
95. The t-butyl ester of phenylglycine tetrahydro-IsoM-4 carboxylate.
96. The pentyl ester of phenylglycine tetrahydro-IsoM-4 carboxylate.
97. The isopentyl ester of phenylglycine tetrahydro-IsoM-4 carboxylate.
98. The t-pentyl ester of phenylglycine tetrahydro-IsoM-4 carboxylate.

Of the compounds of the invention, the most preferred are the sodium salts, i.e. Compounds Nos. 3 and 4 of the above list.

The compounds of the invention have been found to inhibit cholesterol biosynthesis in the liver and thus may be used for the treatment of hypercholesteraemia or the prevention of arteriosclerosis, in the same way as are the compounds disclosed in U.S. patent application Ser. No. 256,243, filed Apr. 21, 1981 which issued as U.S. Pat. No. 4,361,515, or U.S. patent application Ser. No. 270,846, filed June 5, 1981, and the compounds of the invention show an ability to inhibit cholesterol biosynthesis which is broadly comparable with that exhibited by the compounds disclosed in these two U.S. Patent Applications. However, the compounds of the invention have the significant advantage over the compounds disclosed in the aforementioned U.S. Patent Specifications that they are metabolised with much greater difficulty after administration and are thus less readily deactivated; this means that the activity of the compounds of the invention is more persistent and the compounds are thus expected to be of greater effectiveness.

The compounds of the invention may be administered by any conventional means, for example parenterally (e.g. by subcutaneous, intravenous or intramuscular injection) or orally (e.g. in the form of tablets, capsules, powders or granules). The adult daily dose will, of course, vary, depending upon the age, body weight and condition of the patient, as well as upon the route and times of administration, but, in general, the compounds of the invention are preferably administered in an amount of from 5 to 50 milligrams per day, for adults, in a single dose or in divided doses.

The compounds of the invention may be prepared by a variety of processes, all ultimately starting from M-4 or IsoM-4, which may be prepared as a microbial metabolite of ML-236B, and this, in turn, may be prepared as described in United Kingdom Patent Specification No. 1,453,425. The preparation of M-4 and IsoM-4 from ML-236B is described in more detail in Preparations 1 and 2 hereafter, and is also described in U.S. patent application Ser. No. 270,846, filed June 5, 1981.

METHOD 1

Compounds of formula (I) or (II), that is to say tetrahydro-M-4 or tetrahydro-IsoM-4 lactone or tetrahydro-M-4 or tetrahydro-IsoM-4 carboxylic acid, respectively, may be prepared by catalytic reduction of the corresponding M-4 or IsoM-4 compound in a suitable solvent. The nature of the solvent is not critical, provided that it has no adverse effect upon the reaction. Suitable solvents include, for example, alcohols (such as methanol, ethanol or isopropanol) and ethers (such as tetrahydrofuran), any of which may be used in admixture with water. Examples of suitable catalysts include platinum oxide, rhodium colloids, Raney nickel, nickel boride and palladium, of which platinum oxide is preferred. The reaction is preferably effected at or below ambient temperature, e.g. about 25° C. The hydrogen is preferably employed at atmospheric pressure.

METHOD 2

Compounds of formula (III), that is to say metal salts of tetrahydro-M-4 or tetrahydro-IsoM-4 carboxylic acids, may be prepared, for example, by the method described in United Kingdom Patent Specification No. 1,555,831 for the preparation of metal salts of ML-236B carboxylic acid.

METHOD 3

Amino acid salts of tetrahydro-M-4 or of tetrahydro-IsoM-4, that is to say compounds of formula (IV) in which A represents an amino acid, may be prepared from tetrahydro-M-4 or tetrahydro-IsoM-4, respectively, as described in United Kingdom Patent Specification No. 1,555,831.

METHOD 4

Amine salts of tetrahydro-M-4 or of tetrahydro-IsoM-4, that is to say compounds of formula (IV) in which A represents an organic amine or ammonia, may be prepared from tetrahydro-M-4 or from tetrahydro-IsoM-4 by the method described in Japanese Patent Application No. 56-8696, filed Jan. 23, 1981. This comprises reacting an alkali metal carboxylate of tetrahydro-M-4 or tetrahydro-IsoM-4 such as the sodium carboxylate with a mineral acid (e.g. hydrochloric acid) salt of ammonia or an organic amine in a suitable solvent. The nature of the solvent is not critical, provided that it has no adverse effect upon the reaction, aqueous solvents being preferred. Examples include water itself and mixtures of water with one or more organic solvents, such as alcohols (e.g. methanol or ethanol) or ketones (e.g. acetone). The amount of amine salt is preferably equimolar or a slight molar excess, with respect to the metal carboxylate, e.g. a molar ratio amine salt:metal carboxylate of from 1:1 to 1.2:1. The reaction is preferably effected at a pH value of from 7.0 to 8.5 and a temperature of ambient or below, e.g. from 0° to 10°

C., more preferably from 5° C. to 10° C. After the reaction, the resulting salt may be separated from the reaction mixture by extraction with a suitable solvent, such as ethyl acetate.

METHOD 5

Compounds of formula (V), that is to say esters of tetrahydro-M-4 or tetrahydro-IsoM-4 carboxylic acids, may be prepared by esterification of tetrahydro-M-4 or of tetrahydro-IsoM-4, as described in United Kingdom Patent Specification No. 1,555,831 in relation to the preparation of esters of ML-236B carboxylic acid, by reaction of tetrahydro M-4 or of tetrahydro-IsoM-4 with an alcohol in the presence of a suitable catalyst.

METHOD 6

Compounds of formula (V) may also be prepared by reacting tetrahydro-M-4 carboxylic acid or tetrahydro-IsoM-4 carboxylic acid with a diazo compound, preferably diazomethane or a C-substituted diazomethane, as described in United Kingdom Patent Specification No. 1,555,831.

METHOD 7

Tetrahydro-M-4 lactone and tetrahydro-IsoM-4 lactone may be converted to the corresponding carboxylic acids by neutralisation.

The compounds of the invention exist in the form of trans and cis isomers, depending upon the relative orientations of the hydrogen atoms at the 4a and 8a positions of the perhydronaphthalene system. The trans isomer may be represented by the formula

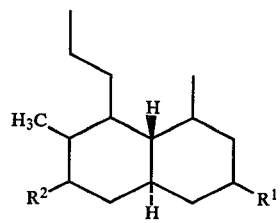

and is generally obtained in the form of crystals, whilst the cis isomer may be represented by the formula:

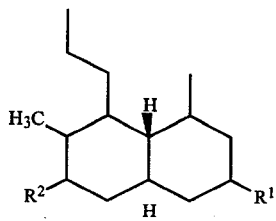

and is generally obtained in the form of an oil. The present invention envisages both the individual isomers and mixtures thereof.

The inhibitory activities against cholesterol biosynthesis of the trans isomers are far stronger than the activities of the corresponding cis isomers.

The compounds of the invention can also exist in the form of various optical isomers and the present invention envisages both the individual isomers and mixtures thereof.

The preparation of the compounds of the invention is illustrated by the following non-limiting Examples, whilst the preparation of M-4 and IsoM-4, the starting materials for the preparation of the compounds of the invention, is illustrated in the following Preparations 1 and 2.

PREPARATION 1

Preparation of IsoM-4

Twenty 500 milliliter Sakaguchi flasks, each containing 100 milliliter of a medium having the composition described below, were innoculated with spores of *Absidia coerulea* IFO 4423. The flasks were subjected to shaking culture at 120 strokes per minute (s.p.m.) and 26° C. for 2 days. At the end of this time, the sodium salt of ML-236B was added to each of the flasks to a final concentration of 0.05% w/v. Cultivation was continued at 120 s.p.m. and 26° C. for a further 5 days.

The composition of the medium was (percentages are w/v):

| | |
|---|---|
| Glucose | 2.0% |
| $K_2HPO_4$ | 0.15% |
| $MgSO_4.7H_2O$ | 0.15% |
| $NH_4NO_3$ | 0.1% |
| Peptone | 0.1% |
| Corn steep liquor | 0.2% |
| Yeast extract | 0.1% |
| $ZnSO_4.7H_2O$ | 0.001% |
| Tap water | the balance |
| (Adjusted to pH 7.0). | |

After completion of the cultivation, the reaction liquor was filtered and the pH of the filtrate was adjusted to a value of 3 by the addition of trifluoroacetic acid. The resulting mixture was then extracted with three 1 liter portions of ethyl acetate, to give extracts containing M-4 and M-3, as well as the desired IsoM-4. The combined extracts were washed with a saturated aqueous solution of sodium chloride and the evaporated to dryness to give a powder containing the lactones of the three compounds.

This powder was then subjected to column chromatography using a Lobar column (Merck Si 60, size A) and the IsoM-4 lactone fraction was eluted using a 1:1 by volume mixture of benzene and ethyl acetate. Evaporation of the solvent yielded 198 milligrams of IsoM-4 lactone, which was further purified using a Lobar column (Merck RP-8, size A), eluted with 35% v/v aqueous acetonitrile, to give 82 milligrams of pure IsoM-4 lactone, having the following characteristics:

1. Nuclear magnetic resonance spectrum:

The nuclear magnetic resonance spectrum measured at 100 MHz in deuterochloroform using tetramethylsilane as the internal standard is shown in FIG. 1 of the accompanying drawings.

2. Ultraviolet absorption spectrum (methanol solution) $\lambda_{max}$ nm:
   229, 234.8, 244.5.

Figure 2:
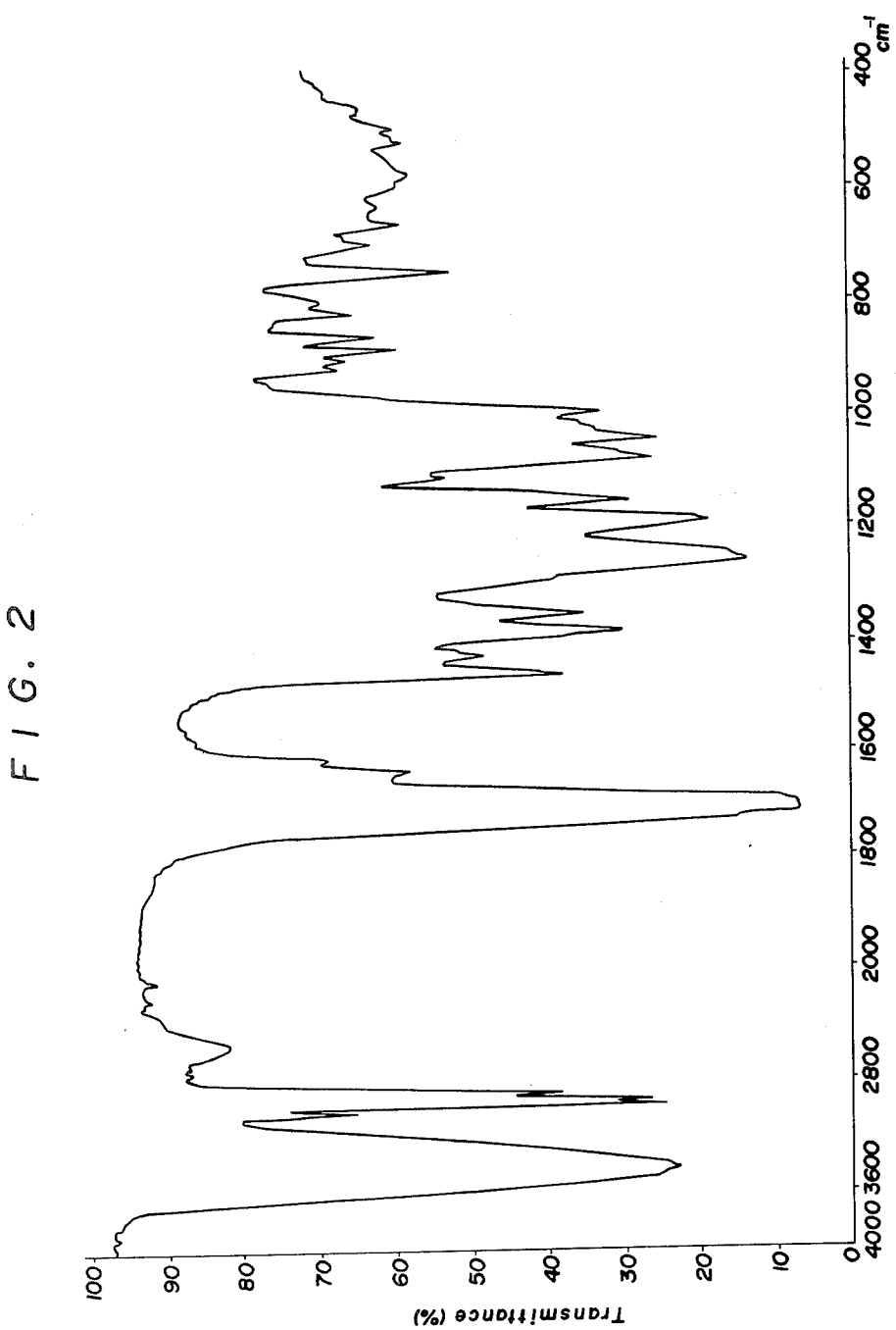

3. Infrared absorption spectrum (thin film):

The infrared absorption spectrum is shown in FIG. 2 of the accompanying drawings.

PREPARATION 2

Preparation of M-4

The procedure described in Preparation 1 was carried out up to and including elution of the first-mentioned Lobar column. After elution of the IsoM-4 lactone with the 1:1 by volume mixture of benzene and ethyl acetate, a further quantity of the same solvent mixture was used to elute the M-4 lactone, taking advantage of the difference in retention times between M-4 and IsoM-4. The resulting M-4 lactone solution was then treated as in Preparation 1, to give 98 mg of the desired M-4 lactone, having the following characteristics:

1. Nuclear magnetic resonance spectrum:

The nuclear magnetic resonance spectrum measured at 60 MHz in deuterochloroform using tetramethylsilane as the internal standard is shown in FIG. 3 of the accompanying drawings.

2. Ultraviolet absorption spectrum (methanol solution) $\lambda_{max}$ nm:
230, 236.7, 244.6.

3. Infrared absorption spectrum (thin film) $\nu_{max}$ cm$^{-1}$:
3400, 2950, 1725.

4. Thin layer chromatography:
TLC plate: Merck silica gel Art 5715:
Solvent: benzene, acetone, acetic acid (50:50:3 by volume);
Rf value: 0.62.

EXAMPLE 1

Tetrahydro-M-4 lactone

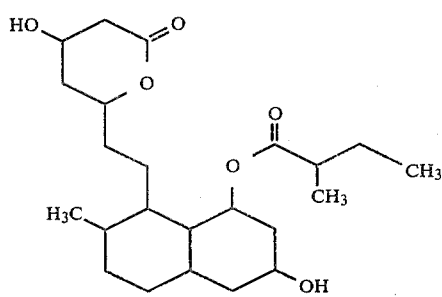

1.05 gram of M-4 was dissolved in 50 milliliters of ethanol, and then 50 milligrams of platinum oxide were added thereto. Hydrogen was then bubbled through the solution at room temperature and under atmospheric pressure until absorption ceased, thus indicating that the catalytic reduction reaction had gone to completion. The catalyst residue was filtered from the reaction mixture and then the filtrate was concentrated by evaporation under reduced pressure to give about 1.1 g of an oily substance. This was purified using a Lobar column RP-8, eluted with 70% v/v aqueous methanol, to give 490 milligrams of crystals which, upon recrystallisation from a 1:2 by volume mixture of hexane and ethyl acetate, afforded 280 milligrams of the desired tetrahydro-M-4 lactone (a mixture of cis and trans isomers), melting at 143° C.

Elemental analysis: Calculated for $C_{23}H_{38}O_6$: C, 67.29%, H, 9.33%. Found: C, 66.98%, H, 9.01%.

Infrared absorption spectrum (KBr) $\nu_{max}$ cm$^{-1}$: 3400, 1720, 1705.

Nuclear magnetic resonance spectrum (60 MHz, CDCl$_3$)$\delta$ppm:
5.3 (1H, doublet);
4.6 (1H, multiplet);
4.3 (1H, multiplet);
3.1 (1H, multiplet);
2.8 (2H, multiplet).

EXAMPLE 2

Methyl tetrahydro-M-4 carboxylate

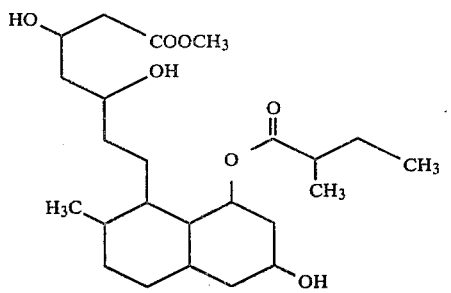

40 milligrams of tetrahydro-M-4 were dissolved in a 0.1N aqueous solution of sodium hydroxide. The pH of the resulting solution was then adjusted to a value of 3 by the addition of trifluoroacetic acid, and then the solution was extracted with ethyl acetate. The ethyl acetate extract was concentrated by evaporation under reduced pressure, after which 1 milliliter of an ethereal solution containing 3 mmole of diazomethane was added to the residue and the mixture was allowed to react for 1 hour at ambient temperature. The product was then purified using a Lobar column RP-8, eluted with a 1:1 by volume mixture of benzene and ethyl acetate, to give 30 milligrams of the desired methyl tetrahydro-M-4 carboxylate (a mixture of cis and trans isomers) in the form of an oil.

Elemental analysis: Calculated for $C_{24}H_{42}O_7$: C, 65.13%; H, 9.57%. Found: C, 64.99%; H, 9.38%. Molecular Weight: 442 (by mass spectrum).

Infrared absorption spectrum (liquid film)$\nu_{max}$ cm$^{-1}$: 3400, 1725.

Nuclear magnetic resonance spectrum (60 MHz, CDCl$_3$)$\delta$ppm:
5.3 (1H, broad singlet);
4.3 (1H, multiplet);
3.8 (3H, multiplet);
3.7 (3H, multiplet);
2.5 (2H, doublet).

EXAMPLE 3

Sodium tetrahydro-M-4 carboxylate

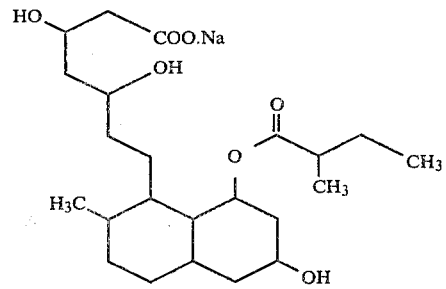

40 milligrams of tetrahydro-M-4 were added to 2.4 milliliter of a 0.04N aqueous solution of sodium hydroxide. The resulting mixture was left to stand at 28° C. overnight, after which it was freeze-dried, affording 40 milligrams of the desired sodium tetrahydro-M-4 carboxylate (a mixture of cis and trans isomers), in the form of an amorphous powder.

Elemental analysis: Calculated for $C_{23}H_{39}O_7Na$: C, 61.33%; H, 8.67%. Found: C, 60.18%; H, 8.32%. Molecular weight: 450 (by field desorption mass spectrum).

Infrared absorption spectrum $(KBr)\nu_{max}$ cm$^{-1}$: 3450, 1730, 1590.

Nuclear magnetic resonance spectrum (60 MHz, $CD_3OD$) $\delta$ppm:
  5.7 (1H, multiplet);
  4.5 (1H, multiplet);
  4.2 (2H, multiplet);
  2.8 (2H, multiplet).

EXAMPLE 4

L-Ornithine tetrahydro-M-4 carboxylate

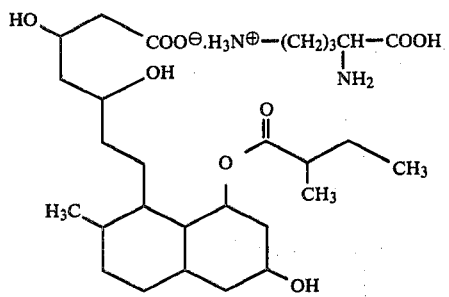

445 milligrams of sodium tetrahydro-M-4 carboxylate were dissolved in 5 milliliter of distilled water, and then 180 milligrams of L-ornithine hydrochloride were added thereto, whilst the pH value of the solution changed from 8.5 to 7.0.

The reaction mixture was then adsorbed on 10 milliliter of a highly porous adsorbent resin (sold under the trade name Diaion HP-20), washed with water and eluted with a 50% v/v aqueous solution of methanol. The eluate was then concentrated under reduced pressure and freeze-dried, to give 550 milligram of L-ornithine tetrahydro-M-4 carboxylate (a mixture of cis and trans isomers), in the form of an amorphous powder.

Elemental analysis: Calculated for $C_{28}H_{52}O_9N_2$: C, 60.00%; H, 9.29%; N, 5.00%. Found: C, 60.51%; H, 9.02%; N, 4.79%.

Infrared absorption spectrum (Nujol-trade mark)$\nu_{max}$ cm$^{-1}$: 3400, 1710.

EXAMPLE 5 t-Octylamine tetrahydro-M-4 carboxylate

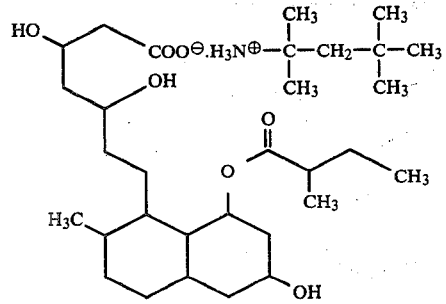

448 milligrams of sodium tetrahydro-M-4 carboxylate were dissolved in 10 milliliters of distilled water and the solution was cooled to 5° C. The pH of the solution was adjusted to a value of 4.0 by the addition of 18% v/v hydrochloric acid and then the solution was immediately mixed with sufficient t-octylamine to raise its pH to a value of 7.5. The reaction mixture was then extracted with ethyl acetate and the extract was concentrated by evaporation under reduced pressure. The residue was mixed with hexane, giving 550 milligrams of the desired compound (a mixture of cis and trans isomers) as a precipitate in the form of a white powder.

Elemental analysis: Calculated for $C_{31}H_{59}O_7N$: C, 66.79%; H, 10.59%; N, 2.51%. Found: C, 66.53%; H, 10.38%; N, 2.66%.

Infrared absorption spectrum (Nujol)$\nu_{max}$ cm$^{-1}$: 3450, 1725.

EXAMPLE 6

Tetrahydro-IsoM-4

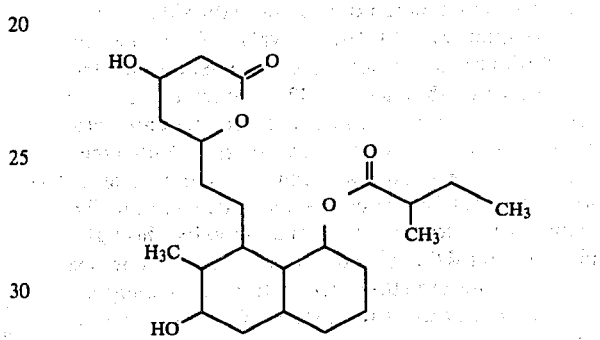

1.1 gram of IsoM-4 was dissolved in 50 milliliters of ethanol, and then 50 milligrams of platinum oxide were added to the solution. Hydrogen gas was then bubbled through the solution at ambient temperature and atmospheric pressure until absorption of the hydrogen ceased, thus indicating that the catalytic reduction reaction had gone to completion. The catalyst residue was filtered from the reaction mixture and the filtrate was concentrated by evaporation under reduced pressure, to give about 1.00 gram of an oily substance. This oily substance was purified by chromatography through a Lobar column RP-8, eluted with 68% v/v aqueous methanol, affording 450 miligrams of the desired compound (a mixture of cis and trans isomers) in the form of an amorphous powder.

Elemental analysis: Calculated for $C_{23}H_{38}O_6$: C, 67.28%; H, 9.33%. Found: C, 67.61%; H, 9.43%. Molecular weight: 410 (by mass spectrum).

Infrared absorption spectrum $(KBr)\nu_{max}$ cm$^{-1}$: 3400, 1720, 1715, 1705.

Nuclear magnetic resonance spectrum (60 MHz, $CDCl_3$) $\delta$ ppm:
  5.1 (1H, singlet);
  4.7 (1H, multiplet);
  4.3 (1H, multiplet);
  3.4 (1H, multiplet);
  2.6 (2H, doublet).

EXAMPLE 7

Methyl tetrahydro-IsoM-4 carboxylate

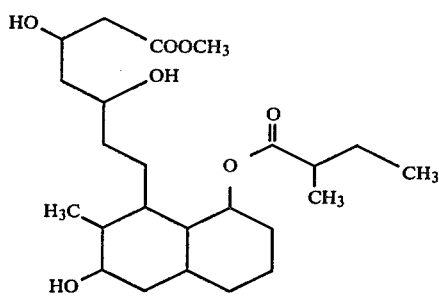

45 milligrams of tetrahydro-IsoM-4 were dissolved in a 0.1N aqueous solution of sodium hydroxide. The pH of the solution was adjusted to a value of 3 by the addition of trifluoroacetic acid, and the mixture was then extracted with ethyl acetate. The extract was concentrated by evaporation under reduced pressure, after which 1 milliliter of an ethereal solution containing 3 mmole of diazomethane was added to the residue and allowed to react for 1 hour at ambient temperature. The product was purified by chromatography through a Lobar column RP-8, eluted with a 1:1 by volume mixture of benzene and ethyl acetate, to give 38 milligrams of the desired product (a mixture of cis and trans isomers), in the form of an oil.

Elemental analysis: Calculated for $C_{24}H_{42}O_7$: C, 65.13%; H, 9.57%. Found: C, 65.28%, H, 9.29%. Molecular weight: 442 (by mass spectrum).

Infrared absorption spectrum (liqud film)$\nu_{max}$ cm$^{-1}$: 3350, 1725.

Nuclear magnetic resonance spectrum (60 MHz, CDCl$_3$) δ ppm:
 5.1 (1H, broad singlet);
 4.2 (1H, multiplet);
 3.8 (1H, broad singlet);
 3.7 (3H, singlet);
 3.3 (1H, doublet);
 2.5 (2H, doublet).

EXAMPLE 8

Sodium tetrahydro-IsoM-4 carboxylate

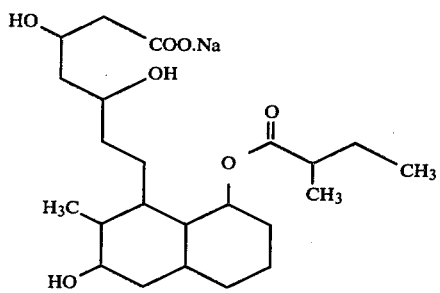

80 milligrams of tetrahydro-IsoM-4 were added to 5.0 milliliter of a 0.04N aqueous solution of sodium hydroxide. The resulting solution was left to stand overnight at 28° C., and then freeze-dried, to give 80 milligrams of the desired product (a mixture of cis and trans isomers) in the form of an amorphous powder.

Elemental analysis: Calculated for $C_{23}H_{39}O_7Na$: C, 61.33%; H, 8.67%. Found: C, 61.78%; H, 8.55%.

Infrared absorption spectrum (KBr)$\nu_{max}$ cm$^{-1}$: 3420, 1725, 1585.

Nuclear magnetic resonance spectrum (60 MHz, CD$_3$OD) δ ppm:
 5.5 (1H, multiplet);
 4.6 (1H, multiplet);
 4.1 (1H, multiplet);
 3.7 (1H, multiplet);
 2.2 (2H, multiplet).

EXAMPLE 9

L-Ornithine tetrahydro-IsoM-4 carboxylate

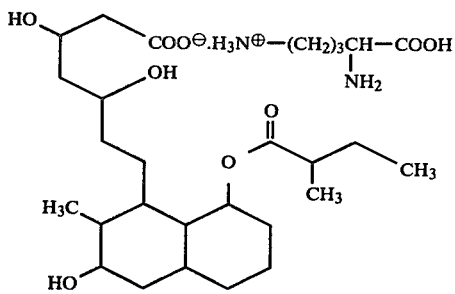

230 milligrams of sodium tetrahydro-IsoM-4 carboxylate were dissolved in 4 milliliters of distilled water, and then 100 milligrams of L-ornithine hydrochloride were added to the resulting solution, whilst the pH value of the solution changed from 8.5 to 7.0.

The resulting mixture was then adsorbed on 8 milliliters of a highly porous adsorbent resin (Diaion HP-20), washed with water and eluted with 50% v/v aqueous methanol. The eluate was concentrated by evaporation under reduced pressure and then freeze-dried, to give 270 milligrams of the title compound (a mixture of cis and trans isomers), in the form of an amorphous powder.

Elemental analysis: Calculated for $C_{28}H_{52}O_9N_2$: C, 60.00%; H, 9.29%; N, 5.00%. Found: C, 61.01%; H, 9.11%; N, 4.87%.

Infrared absorption spectrum (Nujol)$\nu_{max}$ cm$^{-1}$: 3400, 1715.

EXAMPLE 10 t-Octylamine tetrahydro-IsoM-4 carboxylate

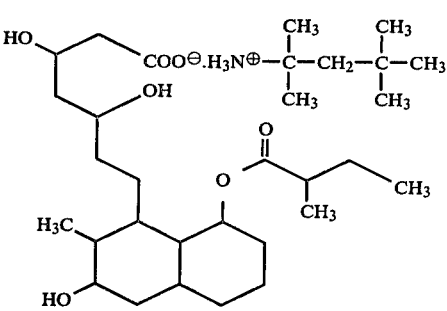

500 milligrams of sodium tetrahydro-IsoM-4 carboxylate were dissolved in 10 milliliters of distilled water, and the resulting solution was cooled to 5° C. The pH of this solution was then adjusted to a value of 4.0 by the addition of 18% v/v hydrochloric acid, and the solution was then immediately mixed with sufficient t-octylamine to give a pH value of 7.5. The resulting mixture was extracted with ethyl acetate and the extract was concentrated by evaporation under reduced reduced pressure. Hexane was added to the residue, giving 570 milligrams of a precipitate of the desired compound (a mixture of cis and trans isomers) in the form of a white powder.

Elemental analysis: Calculated for $C_{31}H_{59}O_7N$: C, 66.79%; H, 10.59%; N, 2.51%. Found: C, 66.48%; H, 10.41%; N, 2.77%.

Infrared absorption spectrum (Nujol)$\nu_{max}$ cm$^{-1}$: 3380, 1720.

EXAMPLE 11

Cis and trans tetrahydro-M-4 lactone 900 mg of M-4 were dissolved in 50 ml of ethanol, and then 30 mg of platinum oxide were added to the solution. Hydrogen was then bubbled through the solution at room temperature and under atmospheric pressure until absorption ceased, thus indicating that the catalytic reduction reaction had gone to completion; this took approximately 5 hours. The catalyst residue was then filtered from the reaction mixture and the filtrate was concentrated by evaporation under reduced pressure. The residue was chromatographed through a Lobar column (Merck Si-60, size B), eluted with 5% v/v acetone in ethyl acetate to give 195 mg of the trans isomer, melting at 143°-144° C.

Using the same system and eluant, 217 mg of the cis isomer, melting at 79° C., were then obtained.

The trans isomer showed an inhibitory activity ($I_{50}$, i.e. the concentration in μg/ml required to inhibit cholesterol biosynthesis by 50%), as measured by the method described in the Journal of Biological Chemistry, 234, 2835 (1959) of 0.0039 μg/ml.

EXAMPLE 12

Sodium tetrahyro-M-4 carboxylate 40 mg of cis-tetrahydro-M-4 lactone obtained as described in Example 11 were dissolved in aqueous acetone, and then 2.5 ml of a 0.04N aqueous solution of sodium hydroxide were added. The resulting mixture was then heated to 40°-50° C. Removal of acetone and freeze-drying then yielded 44 mg of sodium cis-tetrahydro-M-4 carboxylate.

The corresponding trans compound was prepared in the same way from trans-tetrahydro-M-4 lactone and showed an inhibitory activity (by the method referred to in Example 11) of 0.013 μg/ml.

EXAMPLE 13

Methyl trans-tetrahydro-M-4 carboxylate 40 mg of trans-tetrahyro-M-4 lactone, obtained as described in Example 11, were treated with 0.5N aqueous sodium hydroxide and then the solution was neutralised by the addition of trifluoroacetic acid. Further trifluoroacetic acid was then added until the pH of the mixture reached a value of 3. The mixture was then extracted with ethyl acetate. The ethyl acetate extract was then treated with diazomethane, following the procedure described in Example 7 and the mixture was chromatographed using a Lobar column (Merck Si-60, size A) eluted with ethyl acetate, to give 30 mg of methyl trans-tetrahydro-M-4 carboxylate.

We claim:

1. The tetrahydro-M-4 or tetrahydro-IsoM-4 compound of formula (I):

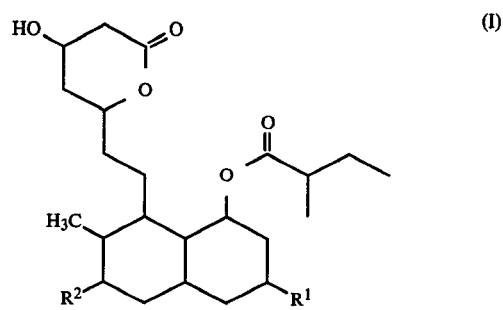

wherein one of $R^1$ and $R^2$ represents a hydrogen atom and the other represents a hydroxy group.

2. The compounds of claim 1 which are in the form of the trans isomers.

3. A lactone selected from the group consisting of the trans and cis tetrahydro-M-4 lactones.

4. The trans tetrahydro-M-4 lactone of the lactones of claim 3.

5. A lactone selected from the group consisting of the trans and cis tetrahydro-IsoM-4 lactones.

6. The trans tetrahydro-IsoM-4 lactone of the lactones of claim 5.

7. A pharmaceutical composition comprising an effective amount of an antihyperlipaemic agent, in admixture with a pharmaceutically acceptable carrier or diluent, wherein the antihyperlipaemic agent is a tetrahydro-M-4 or tetrahydro-IsoM-4 compound of formula (I):

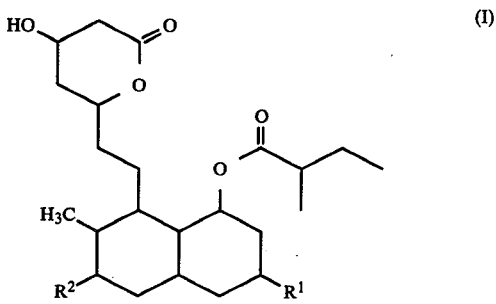

wherein one of $R^1$ and $R^2$ represents a hydrogen atom and the other represents a hydroxy group and wherein said compound is in the form of the trans isomer or the cis isomer or mixtures thereof.

8. The composition of claim 7 wherein said lactones are in the form of the trans isomers.

9. The composition of claim 7, wherein said antihyperlipaemic agent is selected from the group consisting of the trans and cis tetrahydro-M-4 lactones.

10. The composition of claim 9 wherein said lactones are in the form of the trans isomers.

* * * * *